(12) United States Patent
Roeraade et al.

(10) Patent No.: US 7,153,695 B2
(45) Date of Patent: Dec. 26, 2006

(54) CONTINUOUS FLOW TITRATION

(75) Inventors: Johan Roeraade, Tumba (SE); Matthew Rice, Göteborg (SE)

(73) Assignee: Akzo Nobel N.V., Arnhem (NL)

(*) Notice: Subject to any disclaimer, the term of this patent is extended or adjusted under 35 U.S.C. 154(b) by 0 days.

(21) Appl. No.: 10/097,643

(22) Filed: Mar. 15, 2002

(65) Prior Publication Data
US 2003/0032195 A1 Feb. 13, 2003

Related U.S. Application Data

(63) Continuation of application No. 60/276,299, filed on Mar. 16, 2001.

(51) Int. Cl.
*G01N 31/16* (2006.01)

(52) U.S. Cl. ............................. 436/163; 436/148

(58) Field of Classification Search ............... 436/163, 436/148
See application file for complete search history.

(56) References Cited

U.S. PATENT DOCUMENTS 3,654,959 A * 4/1972 Kassel .................. 137/605
3,661,699 A * 5/1972 Farley .................. 162/65
3,674,672 A 7/1972 Whitesell .............. 204/195 R
3,899,294 A 8/1975 Magiros ................ 23/230 A
2002/0151080 A1 * 10/2002 Dasgupta et al. .......... 436/55

FOREIGN PATENT DOCUMENTS

DE 2001707 9/1970

* cited by examiner

*Primary Examiner*—Yelena G. Gakh
(74) *Attorney, Agent, or Firm*—WRB - IP LLP (57) ABSTRACT

The present invention relates to a method for titration comprising guiding a sample to be titrated through a conduit, adding a reagent to said conduit at at least two entrance positions along said conduit in such a manner that said reagent will react with the sample within at least one individual sector of the conduit, defined as the space between two consecutive entrance positions or a final individual sector defined between a final entrance position and a sample exit point of the conduit, while at least one detection device positioned at the end of each sector of said conduit register the chemical and/or physical status. A pressure difference is provided between the reagent delivery device and the sample conduit such that the pressure difference measured between the reagent delivery device and the end of the final individual sector is controlled to be greater than the total pressure drop between the sample delivery point and the end of the final individual sector. The invention further relates to an arrangement for carrying out said method.

9 Claims, 4 Drawing Sheets

CONTINUOUS FLOW TITRATION

This application claims priority from U.S. Provisional Application No. 60/276,299, filed on Mar. 16, 2001, the subject matter of which is hereby incorporated by reference in its entirety.

TECHNICAL FIELD

The present invention relates, in general, to the field of volumetric analysis, and more particularly to continuous flow titration.

BACKGROUND OF THE INVENTION

Titration is one of the most selective and accurate analytical techniques available for the quantitative determination of soluble chemical compounds. In titrimetry, substances are quantified by measuring the volume of a solution with known concentration of reagent that is required for a defined, chemical conversion with the substance being analyzed. Generally, reagent, herein referred to as the "titrant", is added to the sample until one can determine the point at which the sample is completely consumed by the titrant, herein referred to as the "end-point", by means of a readily measurable change in a physical or chemical property at the end-point e.g. change of colour, pH, conductivity etc. Knowing the volume of sample and titrant added up to the end-point, the concentration of the titrant, and the stoichiometric relationship between the sample and the titrant the concentration of the sample can be calculated.

Classical manual titrations are carried out using a burette to accurately deliver the titrant to a known volume of sample with an indicator that undergoes an easily recognisable colour change at the end-point. Titrant is added drop-wise to the sample, mixing between additions, until a permanent colour change of the sample solution occurs, at which point the volume of titrant consumed is read from the burette. As with most analytical procedures, more than one titration is often required to reduce the chance of error. Consecutive titrations are often carried out faster by the continuous addition of titrant up to an amount just prior to the end-point, followed by precise drop-wise additions of titrant up to the end-point. The initial continuous addition of titrant up to an amount just prior to the end-point is herein referred to as "pre-titration".

In the modern laboratory, manual tirations have largely been replaced by automated systems. Such machines help to reduce the need for laborious procedures and/or specific operator skills, and with the further implementation of robotic sample changers, increased efficiency and throughput can be achieved. Automated laboratory titrators have also been modified to monitor industrial process streams, utilizing either intermittent or continuous sampling techniques. More recently, automated titrations have been greatly miniaturized, allowing greater throughput and titrations have been demonstrated down to femtoliter volumes. However, such systems remain by nature, batch-wise, regardless of the size or throughput of the analyzer.

In order to achieve continuous titration, methods have moved to the flow domain. Generally, such methods comprise two pumps; one pumping the sample while the other delivers the titrant. Commonly, a reaction coil and/or a mixing device is employed to ensure either a partial or a complete chemical reaction between the sample and titrant prior to some form of electronic detection device. The past three decades have seen the introduction of numerous continuous flow titration devices based on this general principle, and of particular interest are the gradient methods. The gradient technique is based on the principle that the flowrate (or concentration) of either the sample or the titrant stream is continuously varied, while other parameters remain constant, providing sample concentration proportional to titrant concentration. While gradient techniques have been shown to adapt well to on-line systems, time is still required to generate a concentration gradient which results in a succession of individual results. True continuous methods should provide a readout or indication of the state of a streaming sample in real time.

According to this definition, a continuous flow titration method has been disclosed by DE-A1-2001 707 (Giacobbo and Marly-le-Grand). Said document suggests a method, where the sample to be titrated is continuously pumped through a capillary and where titrant is added at particular points along this capillary in known amounts. After each consecutive addition of titrant, a complete chemical reaction with the sample occurs until the sample is completely consumed. At the end of each reaction in the capillary, detectors are utilized to indicate the chemical status of the sample. In addition, it is suggested that a continuous pre-dilution or pre-titration is performed on the sample in order to increase the precision of the method.

However, DE-A1-2001 707 does not show any experimental results and the examples described in this document are hypothetical. Experimental work carried out to apply the principle and use of the method described by DE-A1-2001 707 lead to unexpected difficulties. It was discovered that unless all flows (sample as well as titrant) were extremely constant, fluctuating end-points and inconsistent results were observed. The majority of pumps, e.g. peristaltic or piston-driven pumps, produce small variations in flow rate that adversely affected the resulting accuracy of the titrations. DE-A1-2001 707 does not describe how to supply a continuous amount of titrant to the consecutive titrant addition points, other than it is suggested to utilize a pump that pumps the same flow for all ten addition points.

GENERAL DESCRIPTION OF THE INVENTION

The present invention provides solutions to at least some of the problems involved with the prior art. One aspect of the invention is directed to a method for titration comprising guiding a sample to be titrated via a sample inlet through a conduit, adding at least one reagent to said conduit by means of a delivery device at at least two entrance positions along said conduit in such a manner that said at least one reagent can react with the sample within at least one individual sector of the conduit. Each sector respectively is defined as the space in the conduit between two consecutive entrance positions and a final individual sector is defined between a final entrance position and a sample exit point of the conduit, while at least one detection device positioned at or near the end of each sector of said conduit register the chemical and/or physical status of the reacted sample in order to determine an endpoint of the titration. A pressure difference between the reagent delivery device and the sample conduit is provided such that the pressure difference measured between the reagent delivery device and the end or near the end of the final individual sector is greater than the total pressure drop between the sample delivery point and the end or near the end of the final individual sector.

Said reagent is preferably consumed to completion or substantially to completion within said at least one individual sector. The final entrance position is defined as the entrance position that, measured along the conduit, is located furthest away from the sample delivery point.

The chemical and/or physical status of the reacted sample that is registered by the at least one detection device can for example include colorimetric, pH value, conductivity, impedance, viscosity, fluorometric and/or turbidimetric.

Significant changes over prior art have been demonstrated whereby the addition of a pressure drop between the point of reagent delivery and the sample in the titration channel was an unforeseen and still more important feature for other fundamental functions of the present invention, as is explained below. Experimental results demonstrate that this method results in a stable system free from flow disturbances and henceforth a significantly increased accuracy for endpoint determination.

The improved stability gained from this method has also lead to a significant improvement whereby a continuous feed-back control based on a monitoring of the end-point, automatically regulates the ratio of sample to pre-titrating reagent. The present invention allows continuous and automatic titration to be performed over a wide range of sample concentrations and conditions with a high degree of accuracy—experimental results demonstrate the ability to accurately, precisely and in real time, titrate a sample which continuously changes in concentration of up to 2.5 orders of magnitude over a 24 hour period of unattended operation.

According to one embodiment of the invention, said pressure difference is controlled to be between 1.5 and 1000000 times greater than the total pressure drop between the sample delivery point and the end or near the end of the final individual sector.

According to a more preferable embodiment, said pressure difference is controlled to be between 2 and 1000 times greater than the total pressure drop between the sample delivery point and the end or near the end of the final individual sector. In an even more preferable embodiment of the invention, said pressure difference is controlled to be between 5 and 50 times greater than the total pressure drop between the sample delivery point and the end or near the end of the final individual sector.

A preferred embodiment of the invention comprises pre-titrating the sample to be titrated with a pre-titration portion of said at least one reagent up to an amount prior to the end point of the titration. Preferably, liquid proportioning valves for delivery of the pre-titration portion of the reagent and the sample can be used, where the flows of said pre-titration portion and said sample art combined prior to entrance into the first sector of the conduit.

Alternatively, a first individual fluid delivery device for delivery of the sample and a second individual fluid delivery device for delivery of the pre-titration portion of the reagent can be used, where the flows from said first and second fluid delivery devices are combined prior to entrance into the first sector of the conduit, while a third separate fluid delivery device is utilized to deliver another portion of the reagent distributed to the remaining entrance positions of the conduit.

A preferred embodiment of the invention comprises keeping the combined flow rate of the sample and the pre-titration portion of the reagent at a constant value.

According to a preferred embodiment of the invention, the proportioning of the sample and the pre-titration reagent is controlled by an electronic control system, preferably a computer, utilizing output signals from the at least one detection device representing the chemical or physical status of the reacted sample at defined positions within the conduit.

A preferred embodiment of the invention furthermore comprises fitting numerical values obtained from the at least one detection device output signals to an explicit mathematical function that follows a general shape of data residing about the endpoint of the titration.

Preferably, the proportioning of the sample and the pre-titration reagent is controlled by implementation of a closed loop feed-back control system.

Said closed loop feed-back control system can preferably include a Fuzzy Logic Controller (FLC).

Another embodiment of the invention furthermore comprises varying the individual proportions of the sample and the pre-titration reagent during the titration, while keeping the flow of reagent distributed to the remaining entrance positions of the conduit constant in order to achieve a dynamic concentration range of titration.

According to another preferred embodiment of the invention, the proportion of the sample to the pre-titration portion of the reagent as well as the reagent distributed to the remaining entrance positions of the conduit are varied during the titration in order to achieve a dynamic concentration range of titration, while the precision of the titration is maximized.

According to a preferred embodiment of the invention, the sample comprises a fluid containing suspended solid material, and wherein the method includes the following steps:
  adding an excess of reagent to said sample,
  removal of said suspended material,
  back-titration of the excess of reagent present in the fluid that remains after the removal of solid suspended material.

Said suspended solid material can preferably be removed by filtration or centrifugation.

According to a preferred embodiment the sample comprises cellulose fibers.

According to further preferred embodiments, the method comprises measuring the electrostatic charge of said cellulose fibers, the electrostatic charge of components in said fluid after removal of said cellulose fibers and/or the kappa number of said cellulose fibers.

The measuring results obtained from the titration procedure are preferably utilized for optimizing dosing of chemicals into the fluid from which the sample is taken.

Said fluid can preferably be pulp or paper stock fluid.

Another aspect of the invention is directed to an arrangement for continuous titration comprising a conduit for guiding a sample, said conduit including a sample inlet and at least two entrance positions for adding at least one reagent by means of a delivery device, such that said reagent can react with the sample within an individual sector of the conduit, wherein each sector respectively is defined as the space in the conduit between two consecutive entrance positions and a final individual sector is defined between a final entrance position and a sample exit point of the conduit. The arrangement further comprises at least one detection device, positioned at or near the end of each sector of said conduit, which detection device registers the chemical or physical status of the reacted sample. The arrangement further comprises means for providing a pressure difference between the reagent delivery device and the sample conduit such that the pressure difference between the reagent delivery device and the end or near the end of the final individual sector is greater than the total pressure drop between the sample delivery point and the end or near the end of the final individual sector.

According to a preferred embodiment of the invention, liquid proportioning valves are arranged for delivery of the sample and of a pre-titration portion of the reagent, whereby the flows of said pre-titration portion and said sample are combined prior to entrance into the first sector of the conduit.

Alternatively, a first individual fluid delivery device can be arranged for delivery of the sample and a second individual fluid delivery device can be arranged for delivery of a pre-titration potion of the reagent, while a third separate fluid delivery device is arranged to deliver another portion of the reagent distributed to the entrance positions of the conduit, whereby the flows from said first and second pumps are combined prior to entrance into the first sector of the conduit.

Said means for providing the pressure difference can preferably comprise narrow bore capillary tubes for delivering the reagent into the conduit.

Alternatively, said means for providing the pressure difference can comprise in-line restrictors positioned near or at the entrance into the conduit.

An important part the invention thus addresses is a basic problem, in cases where particulate material is present either within a sample or whereby the particulate material constitutes the sample. Such samples would rapidly block the titrator conduit and can even interfere with the detection device. However, the present invention presents a novel way for dealing with his problem as described above, whereby reagent is added to the sample in an excess, followed by a removal of the particulate material, e.g. by filtration or centrifugation, followed by a continuous titration of the particulate free sample containing the excess reagent, with a second reagent that titrates the first reagent.

A particular application of this mode of titration, where the combination of the addition of excess reagent, a particle removing step and a continuous titration according to the invention, is for determination of the electrostatic charge of cellulose fibres in pulp and paper slurries used in papermaking. Also determination of the electrostatic charge of other components in said pulp and paper slurries can be undertaken in his way, notably the electrostatic charge of colloidal pitch droplets, fines and chemical additives etc.

Many more parameters of chemical components in pulp and paper process slurries can be determined by the method, including e.g. acidity/alkalinity, ammonia, small ions (calcium, magnesium, aluminium, silica etc), hydrogen peroxide, chlorine dioxide, sulphur and sulphides, starch, polyelectrolytes, chemical oxygen demand, lignin (including Kappa number determination) etc.

Finally, the measured values of the concentration of chemical constituents, obtained with the continuous titration procedure according to the invention, can be utilized to optimise processes, using a closed loop control system to control e.g. chemical dosing equipment. Of particular importance is the procedure, where pulp and paper slurries or white water filtrate (which contains particulate matter) are continuously analysed in the way described above. This would allow a control of the dosing of chemicals to obtain a stable process and optimised fibre retention for optimal paper making.

BRIEF DESCRIPTION OF THE DRAWINGS

The invention will now be described in more detail in the following examples of embodiments with reference to the enclosed drawings wherein.

DETAILED DESCRIPTION OF THE INVENTION

Figure 1:
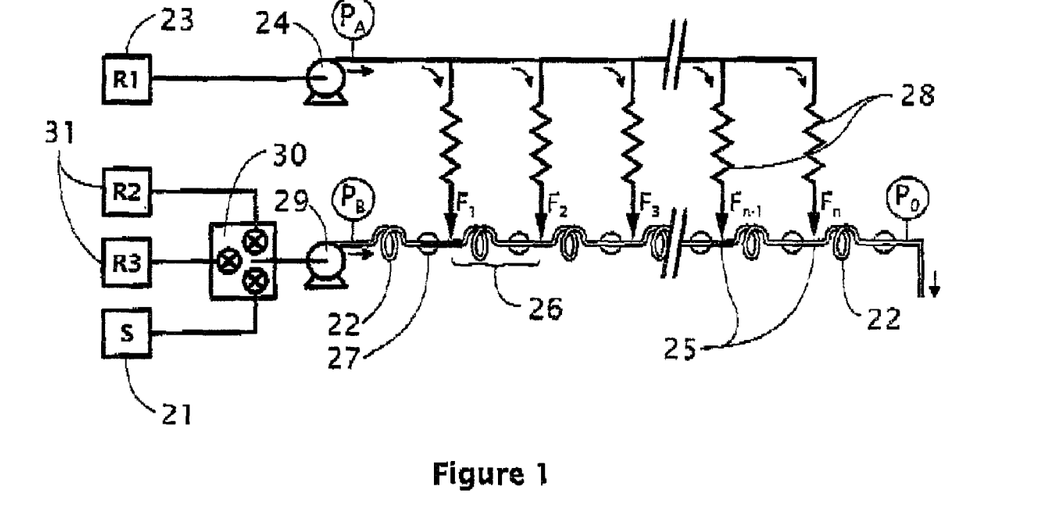
FIG. 1 schematically shows a multiple titrant channel arrangement according to the present invention.

FIG. 1 shows schematically the method according to the invention. The sample to be titrated 21 is guided through a conduit 22 whereby titrating reagent 23 is continuously added to the said conduit by means of a delivery device 24 at a number of pre-defined entrance positions 25 along said conduit in such a manner that the reagent will react with the sample within at least one individual sector 26 of the conduit in such a manner that said reagent is consumed substantially to completion. Each sector 26 of the conduit is defined as the space in the conduit between two consecutive entrance positions. A final individual sector is defined between a final entrance position and a sample exit point of the conduit. Detection devices 27 are positioned near the end of each sector to register the chemical or physical status of the reacted sample.

In order to distribute the titrating reagent 23 to each reagent entrance position 25 in a consistent and defined amount, a large pressure difference between the reagent delivery device 24 and the sample conduit 22 is created. Experimental work showed that said pressure difference, measured between the reagent delivery point $P_A$ and the sample exit point $P_O$ of the conduit, should be greater than the total pressure drop between the sample delivery point $P_B$ and the sample exit point $P_O$ of the conduit in order to achieve consistent results. According to experimental findings, the pressure difference measured between the reagent delivery point $P_A$ and the sample exit point $P_O$ of the conduit ($P_A-P_O$) was shown to be most preferable in the range of 2 to 1000 times greater than the pressure difference across the conduit $P_B-P_O$. Specific details pertaining to the determination and function of this pressure difference relationship are given in Experiment 1.

In order to achieve said pressure drop over an acceptable distance, a suggested method is to utilize lengths of narrow bore capillary tubing 28 connected between the reagent delivery device 24 and each pre-defined entrance position 25. Capillary tubing is beneficial in that the preferred length and bore of these capillaries can be calculated from knowing the desired flow rate and pressure difference required (calculated using Poiseuille's equation).

Alternatively, any device delivering a constant and consistent pressure difference could be utilized, for example in-line flow restrictors such as small bore orifices, a length narrow bore conduit or even a packed column.

A suitable reagent fluid delivery device 24 includes piston type pumps, such as those used for high pressure liquid chromatography (HPLC type) or syringe driven devices, electrokinetic, hydraulic or even reagent delivered from a pressurized reservoir using a gas.

Figure 2:
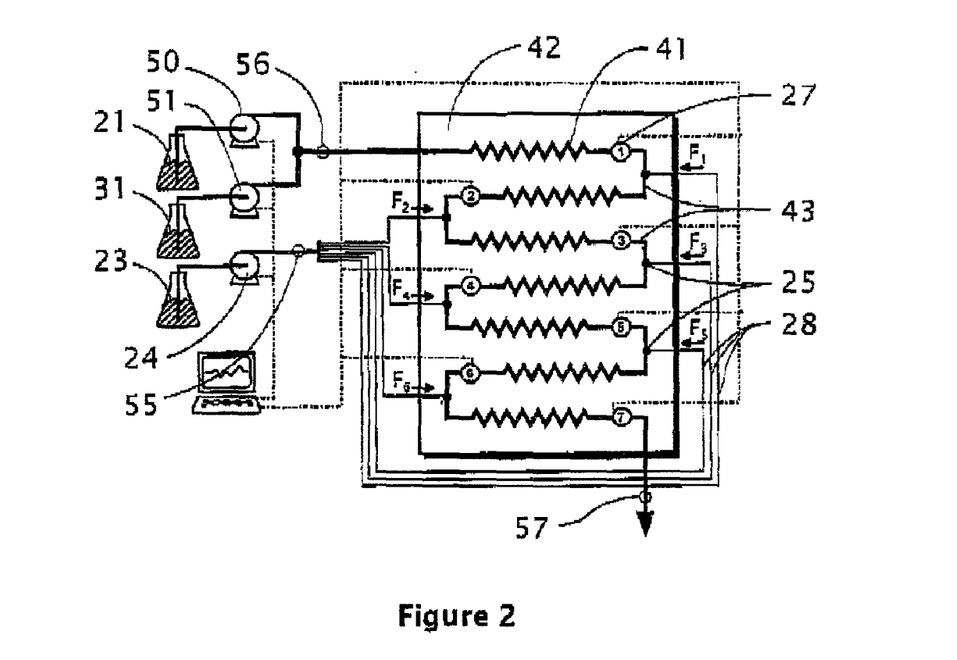
FIG. 2 schematically shows the experimental set-up used in experiments No. 1–3.
Figure 3:
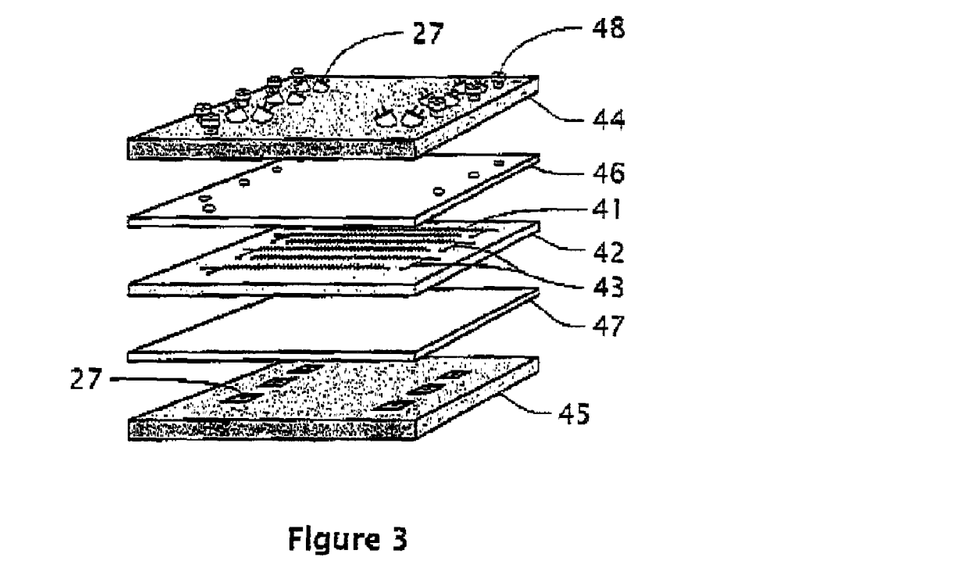
FIG. 3 shows the experimental construction used in experiment No.1.

With reference to FIGS. 2 and 3, the experimental apparatus utilizes a conduit constructed from a zig-zag channel 41 machined into a polymeric material 42, however this design is not limiting. Any structure capable of invoking good contact between the solutes so the reagent is consumed to completion or substantially to completion (dependent upon the reaction kinetics of the specific titration being undertaken) could be utilized. Such devices may be machined or etched channels, tubes, capillaries and other mechanical mixing devices. The experimental apparatus utilized colorimetric detection units, however alternative detection methods include pH, conductivity, impedance, viscosity, fluorometric methods, or even a combination of such devices.

Experimental work has shown that the number of individual sectors required for a reasonable titration and subsequent end-point determination should be limited to a minimum of three sectors. However, greater than five and below twenty sectors would be preferable to ensure a good curve fit. It is also feasible that up to a 100 individual sectors could be utilized, however it must be taken into consideration that the complexity of the apparatus hereby increases.

The entire titrator construction, reagent pressure drop means (flow restrictors), detectors, electronics and fluid delivery devices may be integrated into one structure, for example, a microchip or other monolithic device utilizing e.g. common milling technologies, photolithography and subsequent etching technologies, notably using materials such as silicon, glass or quartz in the form of wafers or chips, or in polymeric materials, where replica technologies such as hot embossing, casting etc can be used, c.f. the fabrication of CD-disks. According to such techniques, it may also be advantageous to produce such a device in a miniaturized format to reduce the consumption of sample for a given titration for applications such as e.g medical and biochemical monitoring of drug metabolites in blood etc.

In combination with the pressure difference between the reagent delivery device 24 and the sample conduit 22, experiments have shown that it is advantageous to operate in a constant pressure mode. Constant pressure conditions within the titrating conduit 22 are achieved by ensuring that the flow rate of titration reagent, controlled by delivery device 24, is constant, in addition to ensuring the combined flow rate of all other fluids entering the conduit remain constant, controlled by a second fluid delivery device 29. The second delivery device 29 may be of the type as that used for the titration reagent.

A pre-titration can be utilized so that the end-point of the titration resides within the range of the further continuous and sequential additions of titrating reagent, a technique analogous to performing a traditional manual titration. In the context of the present invention, it was discovered advantageous to proportion the sample 21 and the "pre-titrating" reagent(s) 31 in such a manner that the combined flow rate remains constant, thus maintaining constant pressures and subsequent flow rates within the conduit 22. Two suggested methods to achieve this proportioning of sample 21 and pre-titrating reagent(s) 31 are:

i) The use of a liquid proportion valve 30 as depicted in FIG. 1. Utilizing this approach, one fluid delivery device 29 can maintain a constant and controlled flow rate while the valves 30 control the proportion of sample 21 and titrating reagent(s) 31 by sequentially opening and shutting in a cyclic and continuous manner—the proportion of each liquid being controlled by the length of time each valve is subsequently open. Such a fluid proportioning device (with pump) is commonly used for quaternary HPLC applications in the analytical laboratory and commercial devices are available for this.

ii) The use of a plurality of fluid delivery devices 50, 51, 24 such as pumps, as depicted in FIG. 2. When a constant combined flow rate is required it should be ensured that the combined flow rate from the pumps remain constant at all times. The individual flow rates of the pumps will control the proportion of sample and titrating reagents. Experiments No. 2, 3 and 4 utilize this specific mode of operation.

By proportioning the sample and pre-titrating reagents in such a manner, in combination with the utilization of said pressure drop, it is possible to greatly expand the titration range of the analyte concentration over existing methods. Practical examples demonstrate that a given concentration of titrating and pre-titrating reagent can titrate a sample varying over three orders of magnitude in concentration, while maintaining a high degree of accuracy and precision at all times. This is further shown in experiment No. 2.

Figure 4:
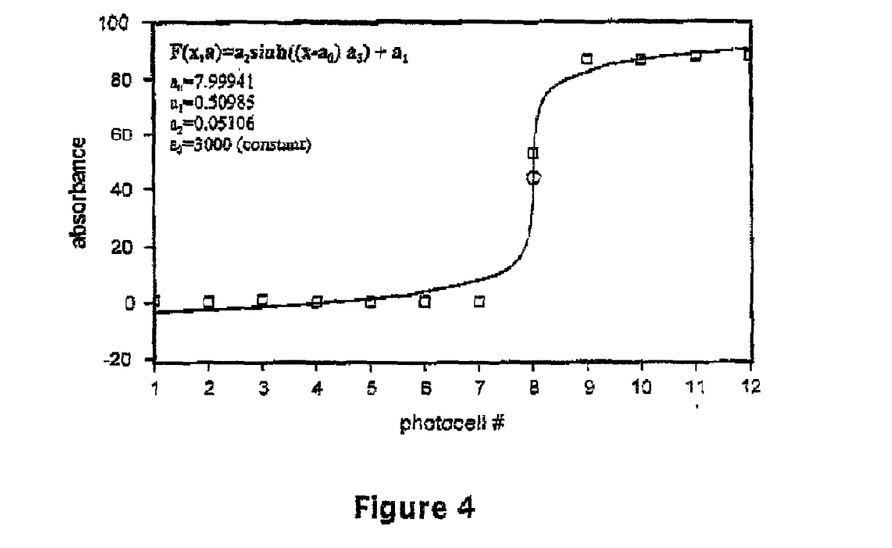
FIG. 4 shows typical titration data with corresponding curve fit with reference to experiment No. 2.

The output signals from the detection devices 27, representing the chemical or physical status of the reacted sample at defined positions within the said conduit, are converted to numerical values that are utilized to determine the end-point of the titration. Common methods of end-point determination from numerical data sets include first and second derivative methods, Gran's plotting, Sevitsky-Golay curve smoothing and fitting the experimental data to derived functions based on explicit expressions describing the specific titration being performed. However, a difficulty experienced with the present invention when applying such methods is that only a small number of data points are produced e.g. between 5 and 20, and such methods were therefore not necessarily always reliable. A new technique, incorporated in the present invention, that is especially suited to the application of small data sets, is to fit the numerical values obtained from the detector output signals to an explicit mathematical function that follows the general shape of data residing about the end-point as a result of the detection device employed and that does not necessarily express the actual physical or chemical phenomena of the titration chemistry. A particularly useful function was found to be, a "S-shaped" inverse hyperbolic since function, whereby a numerical value for the end-point is directly obtained e.g.

$$f(x,a)=a_2 \sin h((x-a_0)a_3)+a_1$$

where coefficient $a_0$ represents the end-point, see FIG. 4. A particularly useful mathematical method to fit the data is the non-linear least-squares Levenberg-Marquardt algorithm. Small data sets are generally between 5 and 20 individual values from the detection devives, however may extend to at least 100 values within the scope of the present invention.

Figure 5:
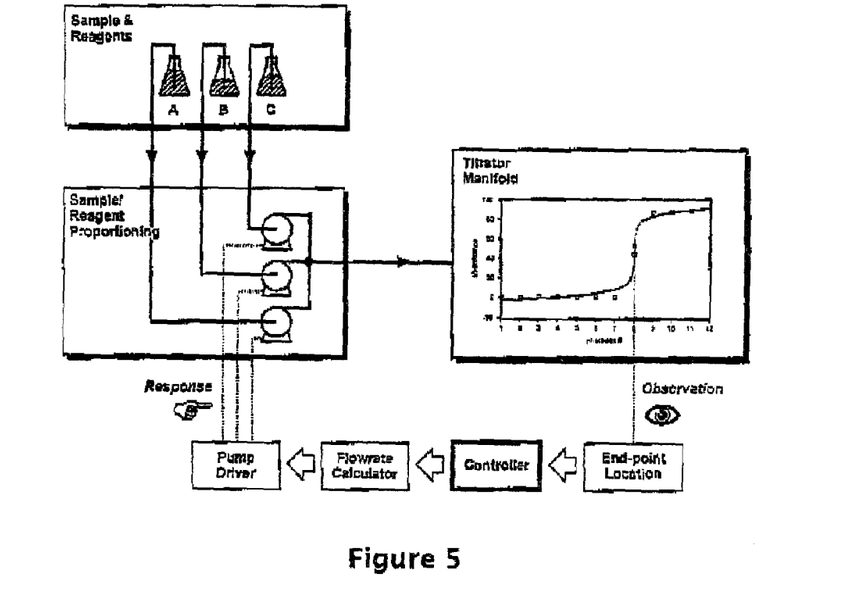
FIG. 5 shows the implementation of the Fuzzy Logic Controller with reference to experiment No. 3.

Furthermore, it was discovered that the pre-titration proportioning of sample 21 and pre-titrating reagent(s) 31 could be automatically and continuously controlled via the implementation of a closed loop feed-back control system based upon knowledge of the location of the end-point in relation to the detection devices employed. The recommended control strategy, utilized as part of this invention, is schematically depicted in FIG. 5. According to the present invention, it was discovered beneficial to keep the end-point centered within the range of the total number of detection devices 27 employed so that both the direction and the magnitude of change in the end-point location could be monitored. For example, in the event of a change in concentration of the sample 21, visualised as a deviation in the location of the end-point from center, a necessary controller response should be to change the proportion of sample 21 and pre-titrating reagent(s) 31 so as to result in a recentering of the end-point. Suitable controllers include proportional (P), proportional integral (PI), proportional integral derivative (PID), artificial intelligence (A.I.) and neural networks. However of particular benefit to the present invention is the use of a Fuzzy Logic Controller (FLC). Furthermore, for the implementation of a such a controller, a computer based system would be preferable. Experiments 3 and 4 demonstrate the application of a Fuzzy Logic Controller for control of the titration device.

It is also feasible that another mode of operation, extending the applicability of the invention is the case, where all flows (the sample flow, the reagent flow used for the pre-titration, as well as the flow to the inlets of the segments) is varied and regulated by a further or additional control method. This particular mode of operation could either continuously, or preferably, so as to keep constant pressure conditions within the apparatus wherever possible, intermittently adjust the flow of said fluid delivery devices 24, 29 so that maximum titration precision can be obtained for different sample conditions.

Experiment 1

Referring to FIG. 1, the effect of varying the said pressure difference ratio measured between the titrant delivery point $P_A$ and the sample exit point $P_0$ of the conduit with respect to the total pressure difference between the sample delivery point $P_B$ and the sample exit point $P_0$ of the conduit is investigated.

The experimental set-up is schematically depicted in FIG. 2 and a simplified representation of the actual experimental construction is given in FIG. 3. The sample conduit 22 was constructed with a zig-zag mixing channel 41 that was machined into a Plexiglass™ board 42 that ensured a thorough mixing of sample with reagent. Additional channels 43 were machined to allow both internal and external fluid transport to and from the mixing channels 41. The Plexiglass™ board 42 was sandwiched between two metal plates 44, 45 and a rubber gland 46, 47 to seal the top of the channels 41 and to mount external fluidic connectors 48 and detection devices 27. The experimental construction provided seven channels (this number was arbitrarily chosen), with each individual channel containing an electronic photometric detection device 27, located between the end of the zig-zag channel and before additional reagent entrance positions, that indicted colour change within the working solution.

Three high pressure HPLC pumps (2150, LKB-Produkter, Bromma, Sweden) 24, 50, 51 were used to pump the operating fluids. The sample pump 50 and the pre-titrating reagent pump 51 was connected directly to the inlet of the first mixing channel, while the titration reagent pump 24 was connected to each reagent entrance position 25 via six lengths of fused silica narrow bore capillary tubing 28. The inner diameter and length of the capillary tubing was chosen depending upon the pressure drop required for the experiment according to Posieuille's equation. The length of the capillary tubing was the same for all six pieces.

In this experiment, all fluids (sample 21 and reagent 23, 31) were water. The flowrate of the titrant stream, measured at point 55, was 0.25 mL.min$^{-1}$, while the flowrate of the sample stream, measured at point 56, was 3.75 mL.min$^{-1}$, producing a combined constant flowrate of 4.00 mL.min$^{-1}$, measured at point 57. Pressure was measured at two points in the arrangement, firstly after the reagent delivery pump 24 and secondly after the sample delivery pump 50. Both measurements were relative to the pressure at point 57 the end of the final sample conduit sector which pressure was atmospheric.

Table 1 shows the results of this experiment, with the flow rates $F_1, F_2 \ldots F_6$ in mL.min$^{-1}$ calculated for each capillary column at various system pressures (bar). The pressure difference ratio $(P_A-P_0)/(P_B-P_0)$ is given at the top of each column.

TABLE 1

Results of experiment 1.

| | | | | | |
|---|---|---|---|---|---|
| $(P_A - P_0)/(P_B - P_0)$ | 2 | 5 | 10 | 100* | 1000* |
| $(P_A - P_0)$ | 13 | 33 | 65 | 654 | 6545 |
| $(P_B - P_0)$ | 6.5 | 6.5 | 6.5 | 6.5 | 6.5 |
| $F_1$ | 0.030 | 0.038 | 0.040 | 0.041 | 0.042 |
| $F_2$ | 0.034 | 0.039 | 0.041 | 0.042 | 0.042 |
| $F_3$ | 0.039 | 0.041 | 0.041 | 0.042 | 0.042 |
| $F_4$ | 0.044 | 0.042 | 0.042 | 0.042 | 0.042 |
| $F_5$ | 0.049 | 0.044 | 0.043 | 0.042 | 0.042 |
| $F_6$ | 0.054 | 0.046 | 0.044 | 0.042 | 0.042 |
| average | 0.042 | 0.042 | 0.042 | 0.042 | 0.042 |
| rel. stdev. | 22% | 7.0% | 3.3% | 0.31% | 0.00% |

*theoretical results as pump pressure was exceeded (400 bar).

This experiment shows that while higher pressure difference ratios provide more evenly distributed titrant flowrates, the pressures required to achieve such ratios become large, e.g a titration reagent pressure of ca. 6500 bar is required to obtain a pressure difference ratio of 1000. Alternatively, a titration reagent pressure of only 13 bars is required to obtain a pressure difference ratio of 2, however the resulting flow rates at each capillary entrance was less evenly distributed (from 0.030 mL.min$^{-1}$ to 0.054 mL.min$^{-1}$). It was possible however to achieve reasonable end point data from the detection devices, and it was also possible to compensate for the uneven distribution of titrating reagent when calculating the amount of reagent consumed at the end-point, so the accuracy of the resulting titrations at this ratio were not affected.

Experiment 2

This experiment looks at the effect of proportioning the sample 21 and pre-titrating reagent 31, the range of the titration apparatus, accuracy and stability.

The experimental set-up is schematically depicted in FIG. 2 and described in Experiment 1, however in this experiment the apparatus utilizes a conduit comprising twelve individual sectors 26 utilizing eleven consecutive titration reagent entrance positions 25 and twelve detection devices 27. The titrating and pre-titrating reagent 23, 31 is 10 mM NaOH with 1×10$^{-5}$ M Bromothymol blue indicator. The titrant flowrate was 0.25 mL.min$^{-1}$, corresponding to an average flowrate of approximately 23 μL.min$^{-1}$ at each consecutive titration reagent entrance position 25, and the combined flowrate of sample 21 and pre-titrating reagent 31 was 3.75 mL.min$^{-1}$. The pressure difference $(P_A-P_0)$ between the reagent delivery point $P_A$ and the sample exit point $P_0$ of the conduit was approximately 70 bar and the pressure difference $(P_B-P_0)$ between the sample delivery point $P_B$ and the sample exit point $P_0$ of the conduit was approximately 14 bars, providing a said pressure difference ratio of approximately 5.

In order to determine a numerical value for the end-point of the titration, the data obtained from the detection devices were fitted to an a sin h function, $f(x,a)=a_2 \sin h((x-a_0)a_3)+a_1$, see FIG. 4. The coefficient $a_3$, corresponding to the slope of the function, was set at a constant value of 3000 and the fitted coefficient $a_0$ was used directly to obtain the location of the end-point with respect to the detection device number (x-axis). For each titration performed, 1000 consecutive titrations were logged and averaged. The sampling frequency of the titration apparatus was approx. 20 Hz which was primarily dependent upon the computer processor being used, and the actual data logging interval was set at ca. 0.4 Hz to reduce to overwhelming amount of data collected from the apparatus.

Table 2 presents the results from the experiment whereby a sulphuric acid sample 21 was continuously titrated. The concentration of sample was 9.72 mM, determined from a manual titration (SD=0.02, n=5). This experiment demonstrates that there exists a range of sample to pre-titrant proportions within the given "window" provided from the twelve detection devices 27 and sequential additions of titration reagent that can be used to locate the end-point. It can be seen that for the continuous titration of the same sulphuric acid sample, the proportion of sample to pre-titrant can range from 0.518 to 0.556 for an end-point value to be obtained from the curve-fitting algorithm. Over this range of operating conditions, the average titrated concentration was 9.744 mM with a relative standard deviation of 0.69%.

TABLE 2

Calculated average titration volumes with standard deviations for varying sample pre-titration ratios for the same sample.

| sample/pre-titrant ratio | average end-point (mL.min$^{-1}$) | SD end-point | concentration $H_2SO_4$ (mM) |
|---|---|---|---|
| 0.518 | 2.515 | 0.006 | 9.825 |
| 0.524 | 2.519 | 0.006 | 9.764 |
| 0.537 | 2.550 | 0.005 | 9.732 |
| 0.543 | 2.556 | 0.006 | 9.681 |
| 0.550 | 2.568 | 0.007 | 9.655 |
| 0.556 | 2.629 | 0.001 | 9.809 |
| average | | | 9.744 |
| relative standard deviation | | | 0.69% |

Table 3 shows the results from the continuous titration of two sulphuric acid samples with substantially differing concentrations in order to demonstrate the function of proportioning of sample 21 and pre-titrant 31. For the given concentration of titrant and pre-titrant (10 mM NaOH), it was possible to titrate a sample of concentration ranging from 0.096 mM to 102 mM. This represents the ability to accurately and precisely titrate a sample varying up to three orders of magnitude in concentration without having to change the concentration of the titrating reagents.

TABLE 3

Titrations performed on samples with differing concentrations.

| manual titration | automatic titration | | |
|---|---|---|---|
| conc. (mM) | sample/pre-titrant ratio | conc. (M) | standard deviation |
| 102 | 0.051 | 104 | 0.722 |
| 0.096 | (no make-up) | 0.094 | 0.0086 |

Experiment 3

This experiment looks at the implementation of a feed back controller in order to automatically control the proportioning of sample and pre-titrating reagent based on a continuous monitoring of the end-point.

The experimental set-up used in this experiment is the same as that used in experiment 2, however the control of the pre-titration is automated by the implementation of a fuzzy logic controller (FLC) based on a monitoring of the end-point, as demonstrated in FIG. 5. The titrating and pre-titrating reagent used was 0.01 M NaOH with $5 \times 10^{-5}$ M Bromothymol blue indicator. The sample was an acetic acid solution whereby the concentration could be either kept constant or varied, either gradually or suddenly, the operator manually determining the rate and extent of the sample concentration change.

Figure 6:
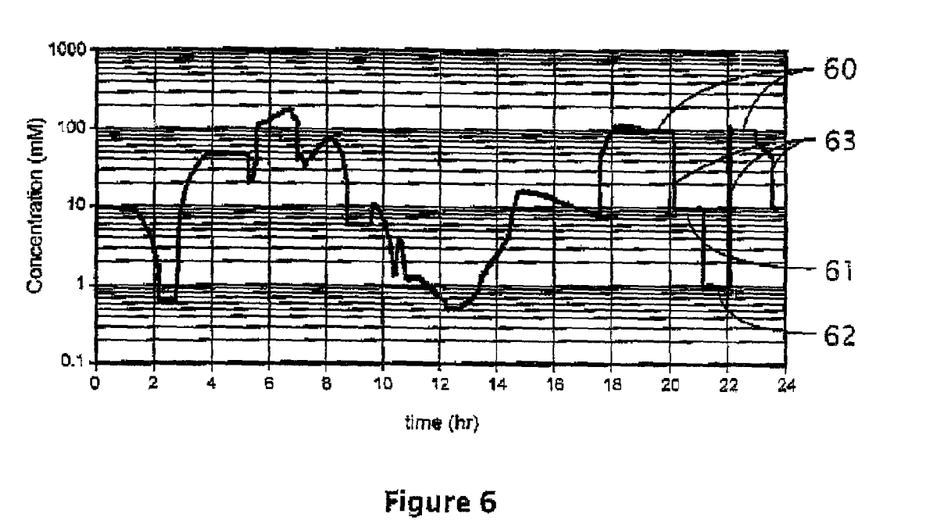
FIG. 6 shows a diagram showing continuous titration of acetic acid over 24 hours with reference to experiment No. 3.

The result of the continuous titration, performed over a period of 24 hours, is given in FIG. 6. During this time interval, 49 297 consecutive titrations were logged. The stability of the FLC and its ability to maintain accurate and fast control was outstanding, even for large and abrupt changes in concentration where the end-point suddenly shifted, requiring large changes 63 in the proportion of sample to pre-titrant in order to re-establish control. An example of such an abrupt change is demonstrated in FIG. 6, whereby a set of standard concentration solutions were used as the sample in a consecutive manner, namely 100 mM, denoted 60 in FIG. 6, to 10 mM, denoted 61, to 1 mM, denoted 62, and then back to 100 mM, denoted 60. The results showed that it was possible to automatically and continuously titrate from ca. 0.5 to 150 mM, with good stability of the end-point and subsequent FLC at both extremes.

Experiment 4

This experiment demonstrates the use of the continuous titration apparatus on a sample containing suspended solid material, namely cellulose fibers, whereby the electrostatic charge of the cellulose fibers is to be analysed. This mode of titration involves adding an excess of reagent to the sample, filtering away the particulate material, followed by a continuous titration of the filtrate that contains the excess reagent that did not react with the sample. A straightforward subtraction yields the amount of chemical that reacted with the sample, in this case representing the fibers charge.

Figure 7:
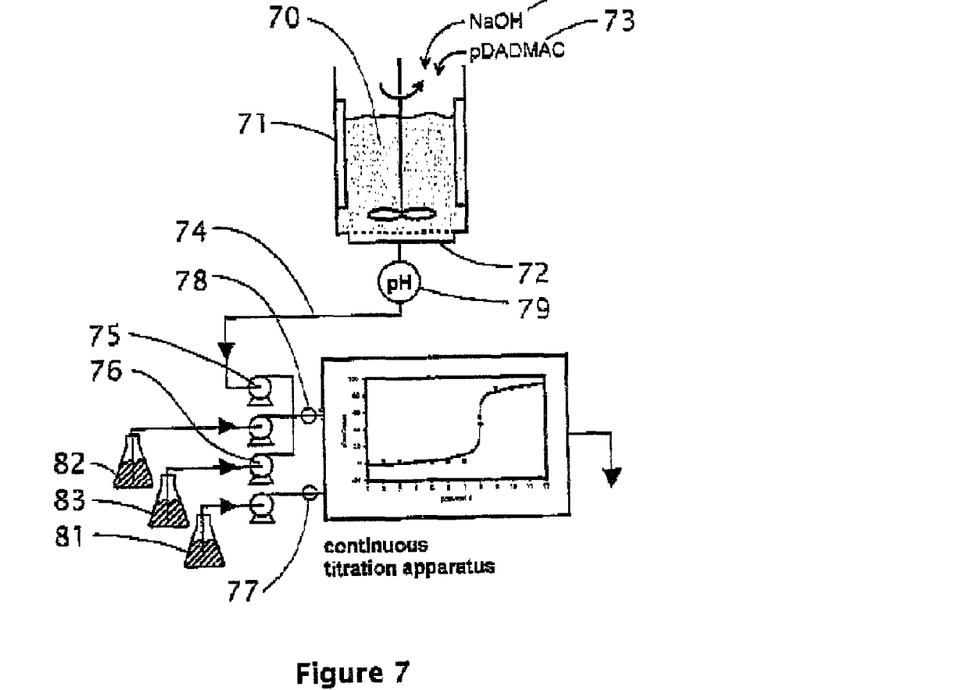
FIG. 7 schematically shows the experimental set-up used in experiments No. 4 comprixing a back titration apparatus for continuous charge titration of a paper furnish.

The experimental set-up is schematically depicted in FIG. 7. The sample 70 comprised of cellulose fibers is stirred in a tank 71 with a filtration membrane positioned at the bottom 72 of the tank. An excess amount of high molecular weight (400 000–500 000) poly-diallyldimethylammonium chloride (pDADMAC) reagent 73 is added to the tank and the excess pDADMAC in the tank, and subsequently the tank filtrate 74 is fed directly to the sample pump 75 of the continuous titration apparatus as described in experiment 3.

In this experiment, the titrating reagent 81 and pre-titrant 82 used is 0.36 mEq.L$^{-1}$ poly(vinylsulfonic acid, sodium salt) and the colorimetric indicator dye 83 was approximately 6.25×10$^{-6}$ M o-toluidine blue (oTB), delivered by using a separate pump 76. The flowrate of titrant was 0.75 mL.min$^{-1}$ 77, utilizing eleven titrant addition points, and the combined flowrate of sample, pre-titrant and indicator dye was 3.25 mL.min$^{-1}$ 78.

To the stirred tank, containing 5 L of a approximately 0.5 weight percent cellulose fiber sample 70, pDADMAC was added to make the tank concentration 0.250 mEq.L$^{-1}$ (before reaction), followed by manually adjusting the tank pH value to 4 with the addition of a 1% sulphuric acid solution. While continuously titrating the tank filtrate, in addition to monitoring the pH value 79, 0.02 M sodium hydroxide solution 80 was constantly added at 3 mL.min$^{-1}$ in order to continuously raise the pH. The experiment was concluded when the pH reached a value of 10 or greater.

Figure 8:
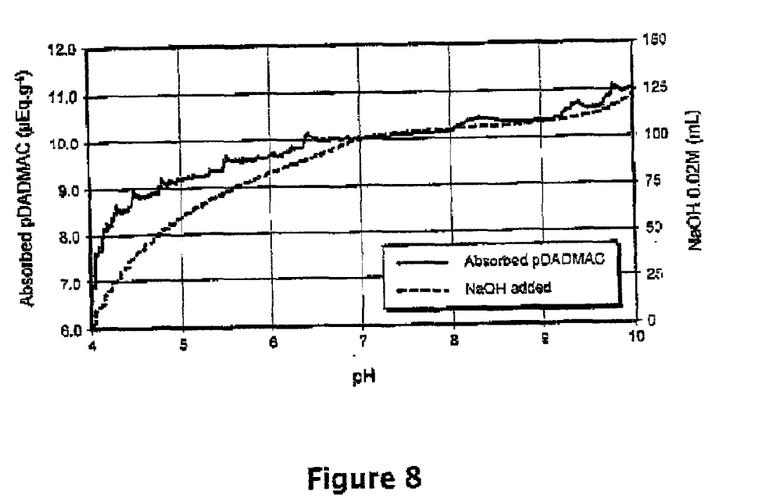
FIG. 8. shows a diagram showing polyelectrolyte absorption with respect to pH value with reference to experiment No. 4.

The results of this experiment are shown in FIG. 8. This experiments is a demonstration of the potential of a suggested mode of operation utilizing the continuous titration apparatus with a sample comprised of particulate material. During this experiment, conducted over a period of approximately 1 hour, 800 separate titrations were logged. From this experiment it can be seen that the greatest change in the fibers charge occurred around pH 4–6, this range probably corresponding to the ionisation of the carboxyl groups present on the fibers surface. The small spikes in the titrated values were related to the FLC, each corresponding to a change in the pre-titration ratio, and were transient in nature.

The invention claimed is:

1. A method for continuous flow titration comprising the steps of:
   continuously delivering a sample to be titrated through a conduit via an inlet at a sample delivery point on said conduit using pressure,
   adding at least one reagent to said conduit by means of a delivery device at at least three entrance positions along said conduit in a consistent and defined amount,
   wherein the consistent and defined amount is provided by creating such pressure difference between the reagent delivery device and the sample conduit that the pressure drop within the conduit becomes insignificant for the results of titration, specifically the pressure difference between the reagent delivery device and the end or near the end of the final individual sector is between 1.5 and 1000 times greater than the total pressure drop within the conduit, that is the pressure drop between the sample delivery point and the end or near the end of the final individual sector; and
   determining a titration endpoint.

2. A method according to claim 1, comprising fitting numerical values obtained from the at least one detection device to an explicit mathematical function that follows a general shape of data residing about the endpoint of the titration.

3. A method according to claim 1, wherein the sample comprises a fluid containing suspended solid material, and where the method includes the following steps:
   adding an excess of reagent to said sample,
   removal of said suspended material,
   back-titration of the excess of reagent present in the fluid that remains after the removal of solid suspended material.

4. A method according to claim 3, wherein the sample comprises cellulose fibers.

5. A method according to claim 1, wherein the step of adding at least one reagent to said conduit comprises the step of passing said at least one reagent through lengths of narrow bore capillary tubing connected between said reagent delivery device and each of said at least three entrance positions.

6. A method according to claim 1, wherein the step of adding at least one reagent to said conduit comprises the step of passing said at least one reagent through a plurality of small bore orifices.

7. A method according to claim 1, wherein the step of adding at least one reagent to said conduit comprises the step of passing said at least one reagent through a packed column.

8. A method according to claim 1, wherein the step of adding at least one reagent to said conduit comprises adding said reagent by means of a piston pump reagent delivery device.

9. A method according to claim 1, wherein the step of adding at least one reagent to said conduit comprises adding said reagent by means of a syringe driven reagent delivery device.

* * * * *